United States Patent
Rosenbloom et al.

(10) Patent No.: US 12,011,446 B2
(45) Date of Patent: Jun. 18, 2024

(54) METHOD OF USING MeK INHIBITOR TO PREVENT RADIATION INDUCED FIBROSIS

(71) Applicant: Thomas Jefferson University, Philadelphia, PA (US)

(72) Inventors: Joel Rosenbloom, Wynnewood, PA (US); Edward John Macarak, Philadelphia, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 735 days.

(21) Appl. No.: 17/049,235

(22) PCT Filed: Apr. 18, 2019

(86) PCT No.: PCT/US2019/028062
§ 371 (c)(1),
(2) Date: Oct. 20, 2020

(87) PCT Pub. No.: WO2019/204569
PCT Pub. Date: Oct. 24, 2019

(65) Prior Publication Data
US 2021/0260066 A1    Aug. 26, 2021

Related U.S. Application Data

(60) Provisional application No. 62/660,392, filed on Apr. 20, 2018.

(51) Int. Cl.
*A61K 31/519* (2006.01)
*A61P 17/16* (2006.01)

(52) U.S. Cl.
CPC ............ *A61K 31/519* (2013.01); *A61P 17/16* (2018.01)

(58) Field of Classification Search
CPC .............................. A61K 31/519; A61P 17/16
See application file for complete search history.

(56) References Cited

U.S. PATENT DOCUMENTS

| | | | |
|---|---|---|---|
| 2003/0055095 A1* | 3/2003 | Baragi | A61K 31/165 514/382 |
| 2005/0049429 A1 | 3/2005 | Barrett et al. | |

FOREIGN PATENT DOCUMENTS

| | | | |
|---|---|---|---|
| WO | 2018009896 A1 | 1/2018 | |
| WO | 2018195392 A1 | 10/2018 | |

OTHER PUBLICATIONS

Wernig, et al., Unifying mechanism for different fibrotic diseases, PNAS, vol. 114, No. 18, 4757-4762 (2017). (Year: 2017).*
Macarak, et al., Trametinib prevents mesothelial-mesenchymal transition and ameliorates abdominal adhesion formation, J. of Surgical Research, vol. 227, pp. 198-210 (2018). (Year: 2018).*
Bellini, A., et al., "The role of the fibrocyte, a bone marrow-derived mesenchymal progenitor, in reactive and reparative fibroses", Lab Invest, vol. 87, No. 9, pp. 858-870, 2007.
Bhattacharyya, S., et al., "Understanding fibrosis in systemic sclerosis: shifting paradigms, emerging opportunities", Nature Reviews Rheumatology, vol. 8, No. 1, pp. 42-54, 2011.
Cheong, Y.C., et al., "IL-1, IL-6 and TNF-alpha concentrations in the peritoneal fluid of women with pelvic adhesions", Hum Reprod, vol. 17, vol. 1, pp. 69-75, 2002.
Duscher, D., et al., "Mechanotransduction and fibrosis", Journal of Biomechanics, vol. 47, No. 9, pp. 1997-2005, 2014.
Falk, P., et al., "Studies of TGF-Beta(1-3) in serosal fluid during abdominal surgery and their effect on in vitro human mesothelial cell proliferation", J Surg Res, vol. 154, No. 2, pp. 312-316, 2009.
Femel, J., et al., "Therapeutic vaccination againstfibronectin ED-A attenuates progression of metastatic breast cancer", Oncotarget, vol. 5, No. 23, pp. 12418-12427, 2014.
Ignotz, R.A., et al., "Transforming growth factor-beta stimulates the expression of fibronectin and collagen and their incorporation into the extracellular matrix", J Biol Chem, vol. 261, No. 9, pp. 4337-4345, 1986.
Ignotz, R.A,, et al., "Regulation of fibronectin and type I collagen mRNA levels by transforming growth factor-beta", J Biol Chem, vol. 262, No. 14, pp. 6443-6446, 1987.
International Search Report and Written Opinion dated Jul. 17, 2019 in International Application No. PCT/US2019/028062 filed Apr. 18, 2019.
Jin, X., et al., "Paradoxical effects of short- and long-term interleukin-6 exposure on liver injury and repair", Hepatology, vol. 43, No. 3, pp. 474-484, 2006.
Jin, X., et al., "Interlcukin-6 inhibits oxidative injury and necrosis after extreme liver resection", Hepatology, vol. 46, No. 3, pp. 802-812, 2007.
Jin, X., et al., "Interleukin-6 is an important in vivo inhibitor of intestinal epithelial cell death in mice", Gut, vol. 59, No. 2, pp. 186-196, 2010.
Jin, X., et al., "Pathobiological mechanisms of peritoneal adhesions: The mesenchymal transition of rat peritoneal mesothelial cells induced by TGF-betaI and IL-6 requires activation of Erk1/2 and Smad2 linker region phosphorylation", Matrix Biology: Journal of the International Society for Matrix Biology, vol. 51, pp. 55-64, 2016.
Kalluri, R., et al., "Epithelial-mesenchymal transition and its implications for fibrosis", The Journal of Clinical Investigation, vol. 112, No. 12, pp. 1776-1784, 2003.
Liu, Q., et al., "A crosstalk between the Smad and JNK signaling in the TGF-peta-induced epithelial-mesenchymal transition in rat peritoneal mesothelial cells", PLoS One, vol. 7, No. 2, Article No. e32009, 9 pages.

(Continued)

*Primary Examiner* — Erich A Leeser
(74) *Attorney, Agent, or Firm* — Cozen O'Connor

(57) ABSTRACT

A method of reducing the severity of radiation induced fibrosis (RIF) by administering to a patient at least a first dose of an MeK inhibitor such as trametinib between 0.01 mg to 2.0 mg, and after said radiation procedure, administering to said patient a further dose of the MeK inhibitor between 0.01 mg and 2.0 mg after the radiation procedure.

10 Claims, 2 Drawing Sheets

(56) References Cited

OTHER PUBLICATIONS

Macarak, E., et al., "Trametinib prevents mesothelial-mesenchymal transition and ameliorates abdominal adhesion", Journal of Surgical Research, vol. 227, pp. 198-210, 2018.
Panahi, F., et al., "Macroscopic and pathological assessment of methylene blue and normal saline on postoperative adhesion formation in a rat cecum model", International Journal of Surgery (London, England), vol. 10, No. 9, pp. 537-541, 2012.
Postlethwaite, A.E., et al., "Cellular origins of fibroblasts: possible implications for organ fibrosis in systemic sclerosis", Current Opinion in Rheumatology, vol. 16, No. 6, pp. 733-738, 2004.
Roberts, A.B., et al., "Transforming growth factor type beta: rapid induction of fibrosis and angiogenesis in vivo and stimulation of collagen formation in vitro", Proc Natl Acad Sci U S A, vol. 83, No. 2, pp. 4167-4171, 1986.
Thiery, J.P, et al., "Complex networks orchestrate epithelial-mesenchymal transitions", NatRevMol Cell Biol, vol. 7, No. 2, pp. 131-142, 2006.
Thiery, J.P., et al., "Epithelial-mesenchymal transitions in development and disease", Cell, vol. 139, No. 5, pp. 871-890, 2009.
Tomasek, J.J., et al., "Myofibroblasts and mechano-regulation of connective tissue remodelling", Nature Reviews Molecular Cell Biology, vol. 3, No. 5, pp. 349-363, 2002.
Wernig, G., et al., "Unifying mechanism for different fibrotic diseases", Proceedings of the National Academy of Sciences of the United States of America, vol. 114, pp. 4757-4762, 2017.
Xu, X., et al., "Role of mast cells and myofibroblasts in human peritoneal adhesion formation", Annals of Surgery, vol. 236, No. 5, pp. 593-601, 2002.

\* cited by examiner

METHOD OF USING MeK INHIBITOR TO PREVENT RADIATION INDUCED FIBROSIS

CROSS REFERENCE TO RELATED APPLICATIONS

This application claims the benefit of U.S. Provisional Application Ser. No. 62/660,392, filed Apr. 20, 2018, the content of which is hereby incorporated by reference in its entirety.

FIELD OF INVENTION

This application is generally related to methods of treatment of radiation induced fibrosis (RIF).

BACKGROUND OF INVENTION

In abdominal adhesion formation, there are three stages with the first being coagulation, a critical factor in adhesion pathogenesis. Studies have shown that coagulation involves a number of protein factors and reactions which either facilitate or inhibit the ultimate formation of a fibrin clot. While, in many cases, the formation of a clot is essential to limit injury, resolution of the clot, in a timely manner, is necessary to prevent adhesion formation. Thus, the balance between fibrin clot formation and its lysis is critical and provides a rational basis for enhancing clot lysis as a therapeutic strategy. However, in practice, this has proven difficult.

The next stage involves the influx of inflammatory cells consisting of multiple cell types and production of a variety of cytokines and factors and which is elicited by a number of inciting events. This has led to attempts to inhibit inflammation as a therapeutic approach to prevent adhesion or fibrosis formation. By and large, this approach has proven to be unsuccessful.

The final stage in the adhesion process is formation of a connective tissue scar. By and large this stage, which is of critical importance since it is this fibrous scar tissue that causes the most severe complications, has received insufficient attention. This is particularly significant since it is highly likely that connective tissue adhesion formation shares many attributes with fibrotic reactions found elsewhere in the body, including systemic ones such as occur in patients with scleroderma and those affecting individual organs including lung, heart, liver and kidney.

Fibrotic lung fibrosis is characterized by histopathological changes in lung architecture, which is characterized by the replacement of pre-existing alveolar structure by permanent fixed scar tissue. Idiopathic pulmonary fibrosis (IPF), in particular, is a pathology of unknown cause and is a type of interstitial lung disease. It is defined clinically by the radiographic appearance of usual interstitial pneumonia on high-resolution computed tomography (HRCT) scan and/or the histologic appearance of usual interstitial pneumonia upon lung biopsy which cannot be traced to common interstitial lung disease risk factors such as occupational exposures to hazardous materials and either connective tissue or auto-immune diseases.

At the cellular level, it is universally appreciated that a particular cell with unique characteristics, the myofibroblast, is responsible, in all incidences, for the replacement of functioning tissue in affected organs, be it mesothelial cells in the gut, t alveoli in the lung or nephrons in the kidney, for example, with non-functional scar tissue which disrupts the normal architecture of the affected organs, ultimately leading to their dysfunction and failure.

While the underlying etiology of fibrotic diseases is frequently unknown, certain signaling pathways activated by several cytokines and growth factors undoubtedly play key roles in their pathogenesis. There is little doubt that the TGF-β family (TGF-β1, -β2, -β3) is the critical regulator of the fibrotic response. The intracellular transduction pathways following TGF-β binding to its cognate receptors are complex but critically important is the fibrotic response.

It is now well-known that although the causes of fibrotic disorders are diverse and causative mechanisms vary widely, they all share important cellular and molecular common features which provide a framework for therapeutic approaches. The mechanisms by which TGF-β and other cytokines activate fibroblasts and stimulate extracellular matrix (ECM) production are incompletely understood, but clearly involve their overproduction in an uncontrolled fashion by myofibroblasts which appears to involve activation of specific intracellular signaling pathways. The MAP kinase ERK1/2 has been identified as a down-stream target of some activation pathways and thus may have a critical role in the pro-fibrotic response to TGF-β. Because of the critical nature of pathway activation by TGF-β, these pathways are potential targets for therapeutic intervention.

Much more information is needed on the cellular and molecular characterization of pro-fibrotic processes that result in adhesion formation in the gut and thickened respiratory membranes in the lung both of which are examples of tissue scars which prevent normal function. Such characterization is critical in order to formulate novel therapeutic approaches.

As noted, the critical cell in the formation of the scar tissue is the myofibroblast which produces increased amounts of fibrillar collagens as well as other pro-fibrotic proteins such as the fibronectin EDA isoform (FNEDA) and which expresses a-smooth muscle actin (αSMA), a molecular marker of activated myofibroblasts [1], While the origins of myofibroblasts may differ depending on the affected organ and the initiating event, in the abdominal cavity, they may arise through a process of trans-differentiation of mesothelial cells in which these cells lose their specific epithelial phenotypic markers such as expression of E-cadherin and acquire a mesenchymal or myofibroblast c phenotype which include fibronectin EDA and αSMA.

Since its first identification, it has been known that transforming growth factor-13 (TGF-β1), a pleiotropic growth factor with a wide and diverse spectrum of biological activities, plays a key role in fibrotic diseases by mediating the formation of myofibroblasts and stimulating the production of extracellular matrix ECM [2-4], IL-6, another pleiotropic cytokine with a wide range of biological activities. [5-7], in addition to TGF-β, was also found to be elevated in peritoneal fluid during abdominal surgeries [8, 9] thus potentially implicating it in the cascade of events which lead to adhesion formation.

However, fibrosis is not limited to the above abdominal and pulmonary fibrosis formation. Indeed, cancer patients undergoing ionizing radiation therapy, either alone or in combination surgery and/or chemotherapy, face long lasting repercussions due to fibrosis formation that can greatly increase morbidity, even if the cancer is in remission.

SUMMARY OF INVENTION

Disclosed embodiments herein are directed to methods of treatment of radiation induced fibrosis in patients through the administration of trametinib to the patient. Certain embodiments are particularly indicated for reducing the occurrence of, preventing, and ameliorating RIF in tissues adjacent to the area of radiation treatment.

In one embodiment, a method is disclosed for reducing the occurrence of RIF in a patient undergoing a radiation procedure comprising administering to said patient at least a first dose of trametinib before a radiation procedure, and after said radiation procedure, administering to said patient a further dose of trametinib, daily, for at least seven days post-radiation therapy. In certain embodiments, the dose of trametinib is between 0.01 mg to 2.0 mg.

In another embodiment, a method is disclosed for reducing the severity of RIF comprising: administering to said patient at least a first dose of trametinib between 0.0 1mg to 2.0 mg, and after said radiation procedure, administering to said patient a further dose of trametinib between 0.01 mg to 2.0 mg, daily, for at least seven days post-radiation procedure.

In another embodiment, a method is disclosed for reducing the severity of RIF after a surgical procedure comprising: administering to said patient at least a first dose of trametinib between 0.01 mg to 3.0 mg, daily, for at least seven days post-radiation procedure.

In another embodiment, a method is disclosed for treating RIF comprising administering to a patient and effective amount of trametinib. A further embodiment is directed to a method of treating RIF comprising administering to a patient at least a first dose of trametinib of between 0.01 to 2.0 mg, daily, for at least seven days. In certain preferred embodiments, treatment of RIF comprises a dosing structure lasting at least 30 days, at least 60 days, at least 90 days, or as long as radiation therapy is employed, given daily to treat, prevent or slow the formation of, or reduce the formation of RIF.

Any of the previously-mentioned methods blocks a pathway shared by fibrotic responses in other organs such as the lung, liver, kidney, heart and bladder.

A disclosed embodiment includes any one of the preceding methods, wherein a first dose is provided between 0.01 to 2.0 mg, and a second dose, is provided so as to maintain a concentration in the blood plαSMA at a therapeutic levels, wherein at least a second dose is provided at an amount less than said first dose.

Another embodiment includes any one of the preceding methods, wherein the at least first does is provided in at least one administration of between 0.001 mg/kg body weight of said patient and of between 0.025 mg/kg body weight of said patient. In preferred methods comprising a first and second dose, wherein the at least second dose is provided at a dose lower than the at least first dose.

Another embodiment, provides a first dose of trametinib, wherein the at least first dose is between 0.01 to 1.0 mg.

Another embodiment is directed to a method of treating a patient for development of excessive fibrin formation is disclosed, comprising; administering to a patient an effective amount of trametinib suitable to treat said fibrin formation resulting from radiation therapy; taking a sample from said patient and detecting for the presence of αSMA and FNEDA; determining the levels of αSMA or FNEDA to confirm the presence or absence of the presence of myofibroblasts; administering at least an additional second dose of trametinib when αSMA or FNEDA are detected in the sample.

In another embodiment, the effective amount of trametinib is between 0.01 mg to 2.0 mg given to a patient in a 24 hour period.

In another embodiment, the effective amount of trametinib is between 0.001 mg/kg and 0.25 mg/kg body weight.

In another embodiment, a method of treating fibrosis from radiation exposure is disclosed, comprising: taking a biopsy from a patient suspected to have fibrosis; determining the presence of αSMA or FNEDA, administering to said patient an effective amount of trametinib when the presence of αSMA or FNEDA are confirmed in the biopsy sample. In a preferred embodiment, wherein the effective amount of trametinib is give as a pharmaceutical composition of between 0.001 mg/kg to 0.25 mg/kg body weight of said patient.

DETAILED DESCRIPTION OF THE EMBODIMENTS

Figure 1A:
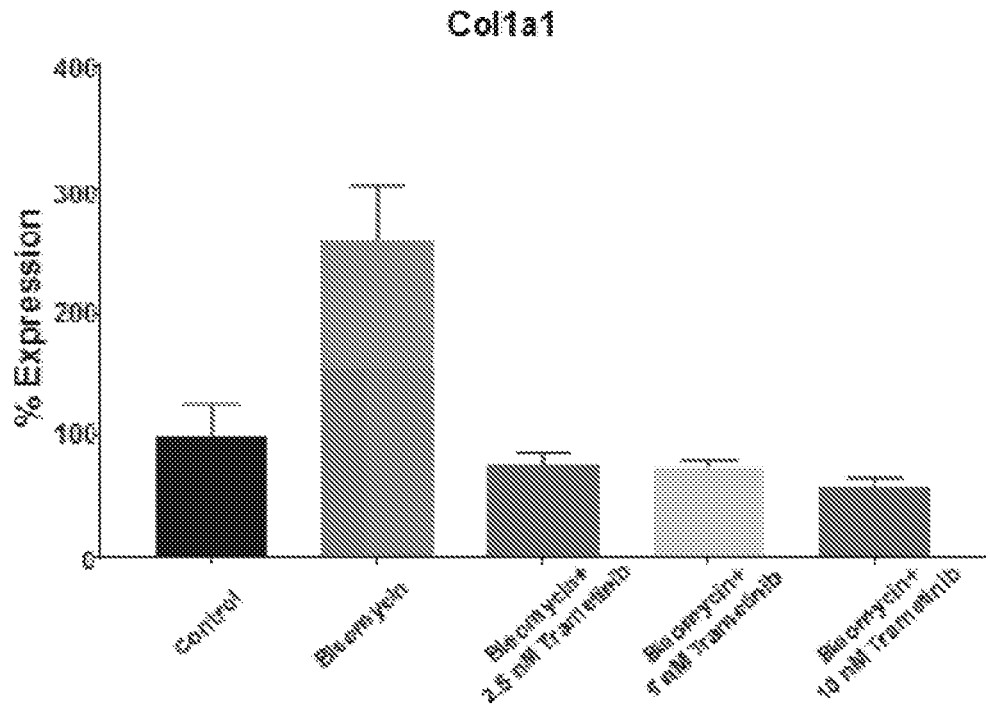
FIGS. 1A, B, and C depict gene expression data for 3 pro-fibrotic genes: Type I collagen, FNEDA, and αSMA in mouse lung fibroblasts treated with bleomycin to induce fibrosis with and without three different doses of trametinib.

The disclosure below provides citations, shown in brackets, e.g. "[10]", which designate references listed prior to the claims below. As used herein, the term "treat" when used in context of treating a disease indicates a delayed onset of disease, reduction in the rate of progression of a disease, reduction in the size of disease formation, reduction on the amount of damaged or diseased tissue. Thus, a treatment may not eliminate all diseased tissue but may stop progression, slow progression, and eliminate some diseased tissue.

As used here, the term "pharmaceutical composition" comprises an active drug ingredient and additional excipients suitable for the particular therapeutic treatment, whether via injection, taken orally, inhalation, or administered to the body cavity via any means known to those of skill in the art. Certain preferred embodiments comprise suitable isotonic injectable, powder or solid or liquids for application to the body, solid or liquid oral forms, nasal, inhalation via aerosols, patches, ointments, solutions, emulsions, and other suitable and known forms for administration.

In our studies, we have determined the effect of the MEK½ inhibitor, trametinib, which is in clinical use in the treatment of malignant melanoma, on the TGF-B induced rat peritoneal mesothelial/mesenchymal transition (MMT) and abdominal adhesion formation in a mouse model. Trametinib effectively blocked the MMT in vitro and markedly diminished adhesion formation in vivo, likely by inhibiting the activation of Erk½ [10], These findings indicate that trametinib may be a useful drug for the inhibition of adhesion formation and warrant human clinical studies [22], C57BL/6 mice were used to develop a consistent model of intra-abdominal adhesion formation. Mouse cecums were gently abraded to promote adhesion formation which were subsequently analyzed histologically and immunochemically to characterize the expression of pro-fibrotic genes including (αSMA and FNEDA isoform, both of which were examined immunohistochemically and by quantitative polymerase chain reaction (qPCR). Trichrome staining was used to assess collagen deposition, a major protein component found in the extracellular matrix (ECM) at adhesion sites. Consistent intra-abdominal adhesions in mice were achieved by gentle cecal abrasion with mortality rates of <10%. Adhesions were seen as early as post-operative day 1 with extensive adhesions being formed and vascularized by day 5. Expression of the FNEDA isoform first and subsequently αSMA and collagen occurred during adhesion maturation.

The drug trametinib was chosen for in vivo studies because prior in vitro studies from our laboratory have demonstrated its effectiveness in blocking the mesothelial-mesenchymal transition (MMT) of rat mesothelium. When the drug trametinib was administered via an osmotic pump implanted during the cecal abrasion surgery, adhesion formation was either absent (no adhesions) or greatly diminished with respect to the initial formation of adhesions as evidenced by the presence of the FNEDA but not αSMA. Thus cecal abrasion is a reliable and reproducible method as a model for generation of intra-abdominal adhesions in mice which can be used to test therapeutic agents capable of blocking the fibrosis associated with adhesion formation. In addition, at the therapeutic doses of trametinib utilized, there was no impairment of the wound healing of the abdominal muscles and skin of the mice at the laparotomy site.

Effect of Trametinib on MMT

Isolated mesothelial cells were incubated under control conditions without either TGF-β or trametinib, with TGF-β or trametinib alone, or with both TGF-β and trametinib for five days. We have previously found that this length of time was required for maximal MMT effect of TGF-β on these rat cells [10], As before, TGF-β produced a dramatic transitional effect, markedly altering the appearance of the cells, while trametinib alone had no effect and no apparent toxic effects with the cells maintaining a cobblestone appearance. Remarkably, trametinib blocked the effect of TGF-β and the cells retained their epitheliod morphologic characteristics.

Based upon our observations, TGF-B-treated cells gained αSMA and Col 1A1 expression and we now show that such gains were prevented by trametinib. These experiments demonstrated that TGF-β produced a substantial increase in the phosphorylation/activation of Erk½ and phosphorylation of the Smad2 linker region as well as increases in expression of αSMA and FNEDA both of which agreed with our preliminary immunofluorescence studies alluded to above. These increases in gene expression of phosphor-Erk½, FNEDA, αSMA and p-SMAD2 (linker) were blocked by as low a concentration of trametinib as 2 nM.

Interestingly, we have identified that cancer patients are highly susceptible to fibrosis formation during and after their cancer treatments. In particular, those receiving radiation therapy are susceptible to fibrosis formation at or around the site of the radiation exposure, indicating damage and thus leading to the fibrosis. While ionizing radiation breaks DNA in the tumor cells potentially killing them, other normal tissue, which are also in the radiation field, sustain damage which leads to significant morbidity. One of the major contributors to the morbidity is radiation-induced fibrosis (RIF), which may occur in the skin and subcutaneous tissue, lungs, gastrointestinal and genitourinary tracts, as well as any other organs in the treatment field. Radiation itself initiates cell and tissue injury leading to chronic inflammation and release of cytokines which ultimately stimulates trans-differentiation of fibroblasts into myofibroblasts. RIF causes excessive proliferation in this population which, in turn, produces excess collagen and other extracellular matrix (ECM) components, which alter tissue architecture and function drastically. The fibrosis associated with RIF alters tissue compliance which, in a majority of cancer patients and particularly those with head and neck cancer, initiates cosmetic and functional impairment that significantly impact quality of life.

Clinical changes associated with RIF usually occurs 4-12 months after radiation therapy and progresses over several years affecting almost every part of the body that is exposed to radiation. Morbidities include skin induration and thickening, muscle shortening and atrophy, limited joint mobility, lymphedema, mucosal fibrosis, ulceration, fistula, hollow organ stenosis, and pain.

The pathogenic mechanism responsible for RIF is similar to that of other types of tissue and organ fibrosis and is mediated by chronic inflammation initiated by the radiation. Subsequent events involve the recruitment and activation of cells which eventually become ECM secreting myofibroblasts. At the cellular level, it is universally appreciated that the myofibroblast is responsible, in all incidences, for the replacement of functioning tissue with scar tissue both in skin and in affected organs, such as in the lung, kidney, heart, etc., ultimately leading to dysfunction and failure. While the underlying etiology of these diseases is frequently unknown, certain signaling pathways activated by several cytokines and growth factors undoubtedly play key roles in their pathogenesis. There is little doubt that the TGF-β family (TGF-β1, -β2, -β3) is the universal critical regulator of the fibrotic response. The intracellular transduction pathways following TGF-β binding to its cognate receptors are complex but critically important is the fibrotic response in RIF.

The mechanisms by which TGF-β and other cytokines activate fibroblasts and stimulate ECM production are incompletely understood, but clearly involve the overproduction of ECM macromolecules in an uncontrolled fashion by myofibroblasts which appears to involve activation of specific intracellular signaling pathways. The MAP kinase ERK ½ has been identified as a down-stream target of some activation pathways and thus may have a critical role in the pro-fibrotic response to TGF-β. Because of the critical nature of pathway activation by TGF-β, these pathways are potential targets for therapeutic intervention.

We have identified that protocols and methods using trametinib as a prophylactic and long term medication, reduce the formation of the biomarkers corresponding to myofibroblast formation, and that effective therapeutic strategies employing trametinib are effective for reducing the formation of or preventing the formation of fibrosis.

DISCUSSION

Radiation induced fibrosis is likely induced through a limited number of cellular and molecular mechanisms responsible for the formation of the scar tissue comprising the fibrosis, irrespective of the cause. The critical cell in this process is the activated fibroblast or myofibroblast which produces increased amounts of fibrillar collagens as well as other ECM components and which expresses αSMA and FNEDA, molecular markers of activated myofibroblasts [14], The accumulation of myofibroblasts and the uncontrolled persistence of their elevated biosynthetic functions are crucial determinants of the extent and rate of progression of fibrotic reactions and of their clinical course, prognosis, and response to therapy.

The origins of myofibroblasts may differ depending on the affected organ and the initiating event, but there are several important potential sources: (i) Activation of tissue resident fibroblasts in response to specific signals from infiltrating inflammatory cells [15]; (ii) Recruitment of bone marrow precursor cells known as fibrocytes which express bone marrow cellular surface markers such as CD34, but are capable of extracellular matrix (ECM) production [15,16]; and (iii) Trans-differentiation of epithelial, mesothelial, and endothelial cells into activated myofibroblasts. Although this process was originally described in epithelial cells and designated epithelial to mesenchymal transition (EMT), it is now known that very similar processes occur in the case of mesothelial (MMT) and endothelial (EndoMT) cells [17-19], In these transitions, the epithelial, mesothelial or endothelial cells may lose their specific markers and traits, such as expression of E-cadherin, and acquire a mesenchymal or myofibroblast phenotype initiating expression of αSMA, vimentin and ECM proteins including FNEDA. One of the hallmarks of the ECM associated with fibrotic diseases is the presence of a contractile myofibroblast. It is currently well-recognized that, regardless of its origin, the resident myofibroblasts in a fibrotic lesion have the cellular protein components to permit force generation. A requirement of this competency is, firstly, the expression of FNEDA. When this occurs, the presumptive myofibroblast is termed a "proto-myofibroblast. It is only later after the proto-myofibroblast expresses αSMA that it is termed a myofibroblast. Without the expression of both these proteins, it not possible for the myofibroblast to transfer force from the interaction of actin and myosin located inside the cell across the cell membrane to the ECM. The fact that the cells in the adhesion expresses only FNEDA and not αSMA suggests that the drug has blocked the conversion of the precursor fibroblast into a functional myofibroblast since both αSMA and FnEDA are required to mediate the transfer of intracellular force to the ECM [20], However, this observation has been quite rare in our studies. Firstly, the occurrence of even presumptive adhesions in the drug-treated animals is a rare event. Entire large intestine bowel from 3 mice for each dose of trametinib were serially sectioned and searched for regions where the intestinal loops were bound to one another. Secondly, when such regions were found, they usually were not developed and were lacking in cellularity. Thus, the rare adhesions which were found were very modest in terms of their molecular composition of biomarkers (αSMA and FNEDA) as compared to those found in untreated animals. No adhesions were found in animals receiving the highest dose.

Theoretically, MMT may be an important cellular mechanism for abdominal adhesions, acting as a source of myofibroblasts. While the origin of the myofibroblasts found in adhesions remains a contentious issue [21], in the present study, we sought to validate our previous findings that the MMT elicited by TGF-β could be blocked by a MEK ½ inhibitor, already in clinical usage for other purposes, and that administering trametinib can be utilized to prevent or reduce the severity of RIF formation after radiation therapy.

The presence of myofibroblasts expressing FNEDA and αSMA are accepted biomarkers of the fibrotic process. Since treatment of animals with the MEK ½ inhibitor trametinib resulted in a significant reduction in expression of these pro-fibrotic biomarkers, these studies indicate that trametinib has therapeutic potential that can be used to block or ameliorate fibrosis not only in the abdominal cavity after surgery but also in the lung and potentially other organs and/or tissues.

Figure 1B:
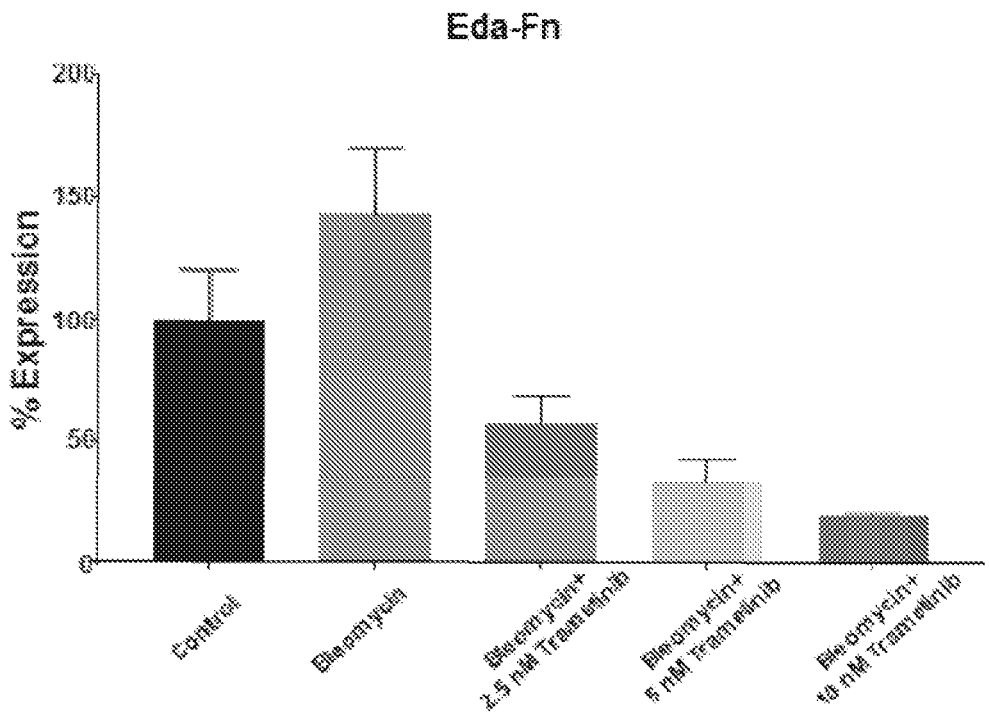
Figure 1C:
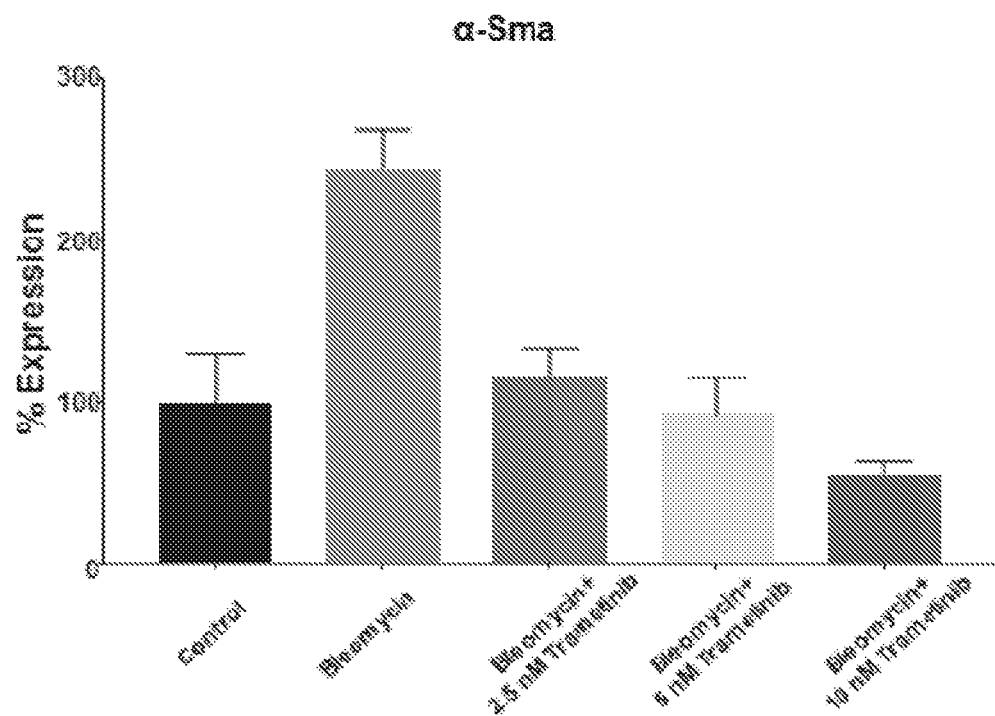

Indeed, FIGS. 1A, 1B, and 1C depict the ability of trametinib to modulate the expression of pro-fibrotic genes in mouse lung fibroblasts. The three graphs represent expression of (type I collagen and FNEDA) and αSMA. Lung fibroblasts isolated form mouse lungs were placed in cell culture and treated either with saline (control) or bleomycin dissolved in saline and 3 different concentrations of trametinib (2.5, 5 and 10 nmolar) dissolved in DMSO. After treatment with the drug, RNA was extracted and quantified by qPCR. mRNAs for type I collagen (Colla1), the FNEDA and αSMA are shown. Control values in FIGS. 1A, B, and C were set to 100%.

As is evident, expression of mRNA for each of the pro-fibrotic genes is dramatically increased for lung fibroblasts treated in vitro with bleomycin as compared to control cells treated with vehicle alone. For Colla1 and αSMAa, an increase in expression of more than 200% is provided, with an increase of nearly 150% for FNEDA. By comparison, expression of these same pro-fibrotic genes in bleomycin-treated lung fibroblasts given 2.5 nM, 5 nM, or 1 OnM of trametinib led to either similar results as to control, i.e. even with the bleomycin, damage either did not accrue, or there was a significant reduction in expression of the pro-fibrotic genes.

Therefore, the results demonstrate that trametinib, a drug presently being used in the treatment of malignant melanoma, was very effective in blocking MMT of rat peritoneal mesothelial cells. This was observed at both the morphological level in which the characteristic cobblestone appearance was maintained and at the molecular level in which the expression of FNEDA and αSMA were inhibited and the phosphorylation of Erk½ was essentially blocked completely. Importantly however, it should be noted, that the concentrations of trametinib used in the present experiments were considerably lower (2 or 5 nM) than that used in experiments involving cultured melanoma cells (100 nM). This suggests that a positive therapeutic response with trametinib could be attained at a much lower dose for treatment and prevention of fibrotic reactions than that required for tumor responses in vivo, minimizing any potential toxic events.

Indeed, this finding of such a low dose is surprising for these cultured lung fibroblast cells. In prior studies for tumor response, the required dose was at least 20× if not 50× the dose required in our applications. Accordingly, the possibility of the therapeutic range being below that for the cultured melanoma cells, provides for a highly useful therapeutic option at otherwise far below therapeutic levels for tumor responses. Administration of low doses may provide a better safety profile as the occurrence of side effects can be limited based on the low dose form to be administered. Furthermore, no prior studies would have suggested that such a low dose form would be therapeutic or be useful, even in cultured cell studies.

This is particularly relevant in the radiation-induced model and methods of treatment that we describe herein. In particular, during radiation therapy, there is a large fibrotic reaction to the treatment site. This is particularly an issue where the fibrosis formation leads to formation of fibrosis that causes morbidity. For example fibrosis that leads to reduction in movement, impairment of muscles or other tissues, or reduction of blood flow or impingement of vascular structure, leads to secondary problems after the radiation treatment. This is extremely difficult for patients, even those who, after treatment, are in remission from the cancer that was original being treated.

For further patients, the fibrosis is damaging in a cosmetic manner. Despite advances in radiation protocols, radiation treatments of head and neck cancers invariably cause damage to surrounding tissues leading to fibrosis in the affected area(s) of the, throat, and larynx. For cosmetic purposes, this leads to complications including loss of facial function and loss of or modification of the larynx.

A method of treatment, therefore is prophylactic in nature, wherein prior to and during the radiation protocol treatment, trametinib is provided as a therapeutic to the patient being treated with radiation. A preferred dose of trametinib for the prophylactic treatment is between 0.001 mg/kg to 0.25 mg/kg body weight. In particular embodiments, it is sufficient to inject a pharmaceutical composition comprising the trametinib into the surrounding tissue for radiation treatment. In other embodiments, a topical pharmaceutical composition comprising the active ingredient can be applied to the area of treatment. In yet other embodiments, the active ingredient is given orally or in other dosage forms suitable for providing the active ingredient to the patient.

A concern arises with regard to the effects of the trametinib on the efficacy of the radiation. However, we have identified that trametinib actually appears to enhance the tumor killing abilities of the radiation. Accordingly, the method of providing trametinib may be able to both treat the fibrosis formation, by preventing or reducing the occurrence of fibrosis due to the radiation treatment, while also providing for a reduced radiation dose needed for the patient to treat and destroy the cancerous cells.

Therefore, the present findings demonstrate that trametinib can effectively inhibit the formation of adhesions due to radiation treatment. Furthermore, this treatment with trametinib is particularly interesting as the effective dosage to inhibit the fibrotic process is much lower than that required in the cancer therapeutic situation. Importantly, our observations also demonstrate that the effective dosage of trametinib had no adverse effect on the effectiveness of radiation treatment, and instead showed the inverse effect and heightened the tumor killing properties in some studies.

Trametinib is typically prescribed at a 1-2 mg dose, once daily for treatment of cancers. For these purposes trametinib is frequently co-administered with a second compound, Dabrafenib, which is taken at much higher dose rates. The studies herein neither require the co-administration protocol nor the concentrations of trametinib as required for cancer treatments.

The trametinib therapeutic therefore may be administered according to the methods as described herein. For example, before a radiation procedure, at least one dose of trametinib can be provided to a patient prior to radiation therapy, wherein the dose is between about 0.01 mg to about 2.0 mg, administering at least one further dose of trametinib at the same or reduced concentration on a daily basis until the risk of radiation fibrosis formation has passed. In certain embodiments, the dose is between 0.01 to about 2.0 mg to a patient. In preferred embodiments, the range is between 0.01 mg to about 1.5 mg, or to about 1.0, 0.75, 0.5, or 0.25 mg, inclusive of all numbers, whether explicitly stated or now. Or, the trametinib can be given at a dose of between 0.001-0.025 mg/kg body weight.

A method of reducing the occurrence of fibrosis owing to radiation treatment, for a patient undergoing radiation therapy procedure comprising administering to said patient at least a first dose of trametinib between 0.01 mg to 2.0 mg, and after said surgical procedure, administering to said patient a further dose of trametinib between 0.01 mg to 2.0 mg, daily, for at least seven days post radiation. Where radiation is given over the course of several periods, the trametinib is advantageously provided before the first radiation procedure and given daily during the entire radiation protocol, and ending about seven days after the last radiation treatment.

In certain embodiments, treatment with trametinib is terminated only after confirmation of certain tests. For example, a test can determine the presence of fibrosis of myofibroblast formation in the patient by testing for the presence of αSMA or FNEDA. Wherein the presence of either or both are identified, treatment with trametinib is indicated. Only after the diminution of these markers is identified, is the treatment tapered off and eventually stopped. Thus, the possibility for fibrosis formation many months after the radiation therapy can be reduced by the maintenance of trametinib treatment until the presence of the αSMA or FNEDA has been extinguished.

A method of reducing the severity of fibrosis formation from radiation therapy comprising: administering to said patient at least a first dose of trametinib between 0.01 mg to 2.0 mg, and after said surgical procedure, administering to said patient a further dose of trametinib between 0.01 mg to 2.0 mg, daily, for at least 365 days post the last radiation therapy procedure. Preferably, the dose is provide between 0.01 mg to 2.0 as an initial dose and a lower dose of between 0.01 mg to 1.0 mg, is provided daily for at least seven days after the last radiation therapy procedure. In certain embodiments a further dose is provided for 250, 200, 180, 150, 120, 90, 60, and 30 days after the last radiation therapy procedure.

A method of reducing the severity of fibrosis formation after radiation therapy comprising: administering to said patient at least a first dose of trametinib between 0.01 mg to 1.0 mg, daily, and thereafter continuing until a test confirms the absence of a biomarker including αSMA or FNEDA, or both. In certain preferred embodiments, prior to radiation treatment, several doses of trametinib are provided to generate a sufficient concentration of the therapeutic in the body.

In certain preferred methods, we can also evaluate the presence of absence of myofibroblasts in a patient by evaluating or detecting the presence of FNEDA or αSMA, or both. Preferably, these markers are detected by measuring the presence in a biopsy taken from the patient. In certain cases, it may be possible to measure FNEDA in plasma whose levels may correlate with disease severity. As well, there are fragments of collagen which may also correlate with disease severity which can also be measured in plasma or urine. Accordingly, testing for the presence of fibrosis or presence of myofibroblasts may include one or all of the above methodologies. The positive detection of fibrosis would then be indicated for treatment with trametinib under the methods of treatment provided herein.

Methods

We tested several molecules for their impact on pathways we believe to be implicated in adhesion. For example, several kinase inhibitors were tested that we believed would implicate and effect the formation of adhesions. However, the non-published data was ineffective. Accordingly, we have omitted data for the compounds that were ineffective.

Reagents and Antibodies

All reagents, unless otherwise specified, were purchased from Sigma (St. Louis, MO). Other reagents were SuperSignal West Pico or Femto Chemiluminescent Substrate and Coomassie Protein Assay (Pierce, Chicago, IL); PVDF membrane (Roche Diagnostics, Basel, Switzerland); #4904, MEK½ #4694, phospho-MEK½ #9154, phospho-Smad2 #3108, phospho-Smad2 (Ser 245/250/255) #3104, p44/42 MAPK (Erk½) #9107, phospho-p44/42 MAPK (Erk½) #4370, antibody to the EDA isoform of fibronectin (FNEDA) and αSMA antibody #ab5694 (Abcam, Cambridge, MA); ImmunoPure peroxidase-conjugated secondary antibodies (Pierce Antibody Products, Waltham, MA); MEK½ inhibitor U0126 (Selleck Chemicals, Houston, TX).

Isolation and Culture of Rat Peritoneal Mesothelial Cells (RPMCs)

The experiments in this study were approved by the Institutional Animal Care and Use Committee at Thomas Jefferson University, and were performed in accordance with the National Institutes of Health guidelines for the care and handling of laboratory animals. RPMCs were isolated and cultured as described previously [12], Briefly, Sprague Dawley rats weighing 150 g-250 g, purchased from Jackson Laboratory, were injected intra-peritoneally with 30 ml of 0.25% trypsin/2.21 mM EDTA under Isoflurane anesthesia and were kept on the metal pad warmed to 37° C. for one hour; after which the abdominal fluid was collected and centrifuged at 300 g for 10 minutes. The isolated pelleted cells were re-suspended and cultured in DMEM/F12 medium supplemented with 10% (v/v) FBS at 37° C. in a humidified atmosphere of 5% CO2 in air. The RPMCs, from the fourth to seventh passages (split ratio 1:4), at 90% confluence were used for the experiments. The cells were treated either with 10 ng/ml of TGF-β1 (R&D systems) alone, or with TGF-β1 and the MEK½ inhibitor, Trametinib (2 or 5 nM).

Cecal Abrasion Model

Equal numbers of male and female C57BL/6 mice (18-25 g, 8-10 weeks of age, Jackson Laboratories, Bar Harbor, Maine) were used in initial experiments while only male mice were used in the drug escalation studies because they sustained greater accumulations of fibrotic tissue (data not shown). Mice were allowed to acclimate in the animal facility for at least one week prior to surgery, given free access to standard chow and water and a 12-h light-dark cycle in standard acrylic cages with wood chip bedding Animals were randomly assigned into either an experimental group (laparotomy and cecal abrasion) or a control group (laparotomy only).

Briefly, mice underwent induction and maintenance anesthesia with 1-3% isofluorane with supplemental oxygen. After adequate sedation was achieved, mice were weighed and 0.1 mg/kg subcutaneous Buprenex (Hospira, Inc., Lake Forest, IL) was administered to ensure analgesia. The ventral surface was clipped along the midline and the skin was sterilized with betadine. A 2 cm midline incision was made subxyphoid to avoid injuring the bladder and the cecum was identified and externalized. The anti-mesenteric side of the cecum was gently swiped 30 times with gauze then returned to the abdomen. The incision was closed with a double layer of sutures with 2-0 silk [13]. To characterize adhesion formation, mice were placed into groups, each with 6 males and 6 females which were necropsied at 1, 2, 5, 8, 11, 14, 17, 21 and 23 days post-surgery. Each time point also contained 2 male mice and one female mouse as controls. In the drug escalation study, laparotomy and cecal abrasion were carried out as above as well as sub-dermal placement of the osmotic pumps.

Drug Treatment with Trametinib

Animals were treated with 3 different doses of the drug trametinib in a dose escalation study. Groups of 5 animals were given 0.1, 1.0 or 3.0 mg/kg animal weight of drug/day via osmotic pumps (Alzet Osmotic Pump 1002, Cupertino, CA) for eight days prior to sacrifice. The volume delivered/day was 6 ul of drug. Control mice underwent induction with anesthesia and laparotomy only. In addition, 5 animals underwent laparotomy and placement of the osmotic pumps which were filled with "drug vehicle (DMSO)" alone i.e., no drug. After 8 days of drug treatment, mice were euthanized under isofluorane anesthesia followed by cervical dislocation. Adhesions were examined by two independent practitioners. The entire large intestine and cecum were removed and partitioned for histology and immunofluorescence microscopy.

Histology

Bowel and abdominal wall involved in the adhesion were removed en bloc and fixed in 4% buffered formalin. Abdominal wall from control mice was also taken as a control. Tissues were dehydrated, embedded in paraffin and sectioned at either 5 or 10 microns (u). Sections were de-paraffinized in a graded ethanol series and stained with Masson's Trichrome. Photographs were taken with a Zeiss light microscope equipped with a Nikon digital camera.

Immunofluorescence

Intestinal tissue was placed in Tissue-Tek O.C.T. Compound (Sakura Finetek, Torrance, CA) and immediately frozen in liquid nitrogen. Frozen sections were cut at either 5 or 10 u, allowed to adhere to albumin-coated slides and then washed with PBS, followed by double staining with goat anti-αSMA polyclonal antibody (1:100, Abcam Inc.), and anti-FNEDA antibody (Anna-Karin Olsson) overnight at 4° C. After washing 3× with PBS, species matched Alexa-Fluor secondary antibodies (Invitrogen) were added and incubated for 1 hr at room temperature followed by 3 washes with PBS. Slides were mounted with DAPI Fluoromount-G (Southern Biotech) and fluorescence images were taken with a Zeiss epi-fluorescence microscope. Controls included omitting the primary antibody and replacing it either with saline or indifferent IgG from a control animal and omission of the secondary antibody. In all instances, controls were either negative or showed very slight non-specific staining with the secondary antibody alone.

Western Blotting Analysis

RPMCs were lysed in ice-cold modified RIPA buffer with protease inhibitor cocktail (50 mM/L Tris-HCl, 1% NP-40, 0.25% Na-deoxycholate, 150 mM/L NaCl, 1 mM/L EDTA, 1 mmol/L phenylmethyl sulfonyl fluoride, 1 mM/L sodium orthovanadate, 1 mM/L NaF, pH 7.4). Equivalent amounts of homogenate (50 μg/well), determined by Coomassie blue assay, were separated by sodium dodecyl sulfate polyacrylamide gel electrophoresis (SDS-PAGE), transferred to either nitrocellulose or PVDF membranes, and detected by SuperSignal West Femto or Pico chemiluminescence.

REFERENCES

1. Tomasek J J, Gabbiani G, Hinz B, Chaponnier C, Brown R A (2002) Myofibroblasts and mechano-regulation of connective tissue remodelling. Nature reviews Molecular cell biology 3 (5):349-363. doi: 10.1038/nrm809
2. Roberts A B, Sporn M B, Assoian R K, Smith J M, Roche N S, Wakefield L M, Heine U I, Liotta L A, Falanga V, Kehrl J H, et al. (1986) Transforming growth factor type beta: rapid induction of fibrosis and angiogenesis in vivo and stimulation of collagen formation in vitro. Proc Natl Acad Sci USA 83 (12):4167-4171
3. Ignotz R A, Massague J (1986) Transforming growth factor-beta stimulates the expression of fibronectin and collagen and their incorporation into the extracellular matrix. J Biol Chem 261 (9):4337-4345
4. Ignotz R A, Endo T, Massague J (1987) Regulation of fibronectin and type I collagen mRNA levels by transforming growth factor-beta. J Biol Chem 262 (14):6443-6446
5. Jin X, Zimmers T A, Perez E A, Pierce R H, Zhang Z, Koniaris L G (2006) Paradoxical effects of short- and long-term interleukin-6 exposure on liver injury and repair. Hepatology 43 (3):474-484. doi:10.1002/hep.21087
6. Jin X, Zhang Z, Beer-Stolz D, Zimmers T A, Koniaris L G (2007) Interleukin-6 inhibits oxidative injury and necrosis after extreme liver resection. Hepatology 46 (3):802-812. doi:10.1002/hep.21728
7. Jin X, Zimmers T A, Zhang Z, Pierce R H, Koniaris L G (2010) Interleukin-6 is an important in vivo inhibitor of intestinal epithelial cell death in mice. Gut 59 (2):186-196. doi:10.1136/gut.2008.151175 gut.2008.151175 [pii]
8. Falk P, Bergstrom M, Palmgren I, Holmdahl L, Breimer M E, Ivarsson M L (2009) Studies of TGF-β eta(1-3) in serosal fluid during abdominal surgery and their effect on in vitro human mesothelial cell proliferation. J Surg Res 154 (2):312-316. doi:10.1016/j.jss.2008.05.012S0022-4804(08)00359-4 [pii]
9. Cheong Y C, Shelton J B, Laird S M, Richmond M, Kudesia G, Li T C, Ledger W L (2002) IL-1, IL-6 and TNF-alpha concentrations in the peritoneal fluid of women with pelvic adhesions. Hum Reprod 17 (1):69-75
10. Jin X, Ren S, Macarak E, Rosenbloom J (2016) Pathobiological mechanisms of peritoneal adhesions: The mesenchymal transition of rat peritoneal mesothelial cells induced by TGF-beta1 and IL-6 requires activation of Erk½ and Smad2 linker region phosphorylation. Matrix biology: journal of the International Society for Matrix Biology. doi:10.1016/j.matbio.2016.01.017
11. Femel J, Huijbers E J, Saupe F, Cedervall J, Zhang L, Roswall P, Larsson E, Olofsson H, Pietras K, Dimberg A, Hellman L, Olsson A K (2014) Therapeutic vaccination against fibronectin ED-A attenuates progression of metastatic breast cancer. Oncotarget 5 (23): 12418-12427. doi: 10.18632/oncotarget.2628
12. Liu Q, Zhang Y, Mao H, Chen W, Luo N, Zhou Q, Yu X (2012) A crosstalk between the Smad and JNK signaling in the TGF-βeta-induced epithelial-mesenchymal transition in rat peritoneal mesothelial cells. PLoS One 7 (2):e32009. doi: 10.1371/journal.pone.0032009 PONE-D-11-21744 [pii]
13. Panahi F, Sadraie S H, Khoshmohabat H, Shahram E, Kaka G, Hosseinalipour M (2012) Macroscopic and pathological assessment of methylene blue and normal saline on postoperative adhesion formation in a rat cecum model. International journal of surgery (London, England) 10 (9):537-541. doi: 10.1016/j.ijsu.2012.08.009
14. Xu X, Rivkind A, Pappo O, Pikarsky A, Levi-Schaffer F (2002) Role of mast cells and myofibroblasts in human peritoneal adhesion formation. Annals of surgery 236 (5):593-601. doi: 10.1097/01.sla. 0000033037.13104.c4
15. Postlethwaite A E, Shigemitsu H, Kanangat S (2004) Cellular origins of fibroblasts: possible implications for organ fibrosis in systemic sclerosis. Current opinion in rheumatology 16 (6):733-738
16. Bellini A, Mattoli S (2007) The role of the fibrocyte, a bone marrow-derived mesenchymal progenitor, in reactive and reparative fibroses. Lab Invest 87 (9):858-870. doi:3700654 [pii] 10.1038/labinvest.3700654
17. Thiery J P, Sleeman J P (2006) Complex networks orchestrate epithelial-mesenchymal transitions. NatRevMol Cell Biol 7 (2): 131-142. doi:nrm1835 [pii] 10.1038/nrm1835
18. Thiery J P, Acloque H, Huang R Y, Nieto M A (2009) Epithelial-mesenchymal transitions in development and disease. Cell 139 (5):871-890. doi: 10.1016/j.cell.2009.11.007 S0092-8674(09)01419-6 [pii]
19. Kalluri R, Neilson E G (2003) Epithelial-mesenchymal transition and its implications for fibrosis. The Journal of clinical investigation 112 (12):1776-1784. doi: 10.1172/jci20530
20. Duscher D, Maan Z N, Wong V W, Rennert R C, Januszyk M, Rodrigues M, Hu M, Whitmore A J, Whittam A J, Longaker M T, Gurtner G C (2014) Mechanotransduction and fibrosis. Journal of biomechanics 47 (9): 1997-2005. doi:10.1016/j.jbiomech.2014.03.031
21. Bhattacharyya S, Wei J, Varga J (2011) Understanding fibrosis in systemic sclerosis: shifting paradigms, emerging opportunities. Nature reviews Rheumatology 8 (1): 42-54. doi: 10.103 8/nrrheum.2011.149
22. Macarak E, Lotto C, Kolganti D, Jin X, Wermuth P, Olsson A-K, Montgomery M and Rosenbloom J. (2018) Trametinib prevents mesothelial-mesenchymal. transition and ameliorates abdominal adhesion. Journal of Surgical Research (In Press, July 2018).

The invention claimed is:

1. A method of reducing the occurrence of radiation exposure fibrosis formation in a patient undergoing radiation therapy comprising administering to said patient an effective dose of one or more MeK inhibitors, sufficient to prevent the formation of an adhesion.

2. The method of claim 1, wherein the one or more MeK inhibitors comprises trametinib, and wherein the effective dose comprises between 0.01 mg to 2.0 mg.

3. The method of claim 2, comprising administering to said patient at least a first dose of trametinib prior to a radiation procedure of between 0.01 to 2.0 mg.

4. The method of claim 3, further comprising administering to said patient at least a second dose of trametinib after said radiation procedure of trametinib between 0.01 mg to 2.0 mg.

5. The method of claim 4, wherein the at least a second dose of trametinib is administered daily, for at least seven days post-surgery.

6. The method of claim 1, wherein the method blocks a pathway shared by fibrotic responses in other organs such as the lung, liver, kidney, heart and bladder.

7. The method of claim 1, wherein a first dose is provided between 0.01 to 2.0 mg, and a second dose is provided so as to maintain a concentration in the blood plasma at a therapeutic levels, wherein at least a second dose is provided at an amount less than said first dose.

8. The method of claim 1, wherein the at least first dose is provided in at least one administration of between 0.001 mg/kg body weight of said patient and of between 0.025 mg/kg body weight of said patient.

9. The method of claim 1, wherein the at least second dose is provided at a dose lower than the at least first dose.

10. The method of claim 1, wherein the at least first dose is between 0.01 to 1.0 mg.

* * * * *